US005798121A

United States Patent [19]

Cauwet et al.

[11] Patent Number: 5,798,121
[45] Date of Patent: Aug. 25, 1998

[54] STABLE COSMETIC, DERMATOLOGICAL OR PHARMACEUTICAL COMPOSITION COMPRISING SELENIUM DISULPHIDE AND AT LEAST ONE ZINC SALT

[75] Inventors: Danièle Cauwet; Henri Sebag, both of Paris, France

[73] Assignee: L'Oreal, Paris, France

[21] Appl. No.: 576,431

[22] Filed: Dec. 19, 1995

[30] Foreign Application Priority Data

Dec. 20, 1994 [FR] France .................. 94 15326

[51] Int. Cl.⁶ .................. A61K 33/32; A61K 33/04; A61K 31/095; A61K 31/19
[52] U.S. Cl. .................. 424/642; 424/641; 424/707; 514/557; 514/706
[58] Field of Search .................. 424/641, 642, 424/707; 514/557, 706

[56] References Cited

U.S. PATENT DOCUMENTS 2,694,669 11/1954 Baldwin et al. .

4,854,333 8/1989 Inman et al. .

FOREIGN PATENT DOCUMENTS 0326272 8/1989 European Pat. Off. .
2587208 3/1987 France .

OTHER PUBLICATIONS

Chemical Abstracts, 116:67223 (1990).

*Primary Examiner*—Zohreh Fay
*Attorney, Agent, or Firm*—Nixon & Vanderhye, P.C.

[57] ABSTRACT

Stable cosmetic, dermatological or pharmaceutical composition comprising, in an aqueous medium, selenium disulphide.

This composition contains, in a mixture with selenium disulphide, at least one zinc salt in an inorganic or organocarboxylic acid.

Method for the treatment of hair, especially against dandruff.

14 Claims, No Drawings

US 5,798,121

STABLE COSMETIC, DERMATOLOGICAL OR PHARMACEUTICAL COMPOSITION COMPRISING SELENIUM DISULPHIDE AND AT LEAST ONE ZINC SALT

The present invention relates to a stable cosmetic, dermatological or pharmaceutical composition which comprises selenium disulphide and at least one zinc salt of an inorganic or organocarboxylic acid as stabilizer. The present invention relates more particularly to an anti-dandruff hair composition.

With a view to combating the formation of dandruff, which is generally accompanied by microbial and/or fungal proliferation, anti-dandruff products which have been proposed include either products which inhibit microbial proliferation or keratolytic products. Among the latter, the use of selenium disulphide has been particularly recommended owing to its powerful cytostatic activity (see Ch. Zviak "Science des traitements capillaires" [Science of hair treatments], Ed. 1988).

Thus EP-0 524 859 proposes the use in shampoos of selenium disulphide in combination with a nonionic surfactant of the alkyl polyglucoside or polyglycerolated type in the presence of a suspension agent chosen from biopolysaccharides or anionic celluloses.

Moreover, EP-0 422 508 describes the use in shampoos of selenium disulphide in association with a salt of 2-mercaptopyridine N-oxide or of 1-hydroxy-2-pyrrolidone in the presence of a nonionic surfactant of the alkyl polyglucoside type.

However, although selenium disulphide has an excellent anti-dandruff activity, it has the disadvantage of gradually becoming brown over time, passing from orange to greenish brown.

In order to overcome this colour change problem, U.S. Pat. No. 4,854,333 proposes compositions which comprise, in combination with selenium disulphide, an oxidizing agent of the peroxide or persalt type. However, the use of oxidizing agents can give rise to problems of toxicity and/or compatibility in the compositions.

It has now been found, surprisingly and unexpectedly, that it is possible to obtain selenium disulphide-based compositions of stable colour, by using, in combination, a zinc salt of an inorganic or organocarboxylic acid.

According to the invention, the term composition of stable colour refers to a composition which, when kept for at least one month in an oven at 45° C., shows no substantial change in colour relative to its initial colour.

The subject of the present invention is therefore a cosmetic, dermatological or pharmaceutical composition which has an anti-dandruff action, is stable and comprises, in an aqueous medium, selenium disulphide in a mixture with at least one zinc salt of an inorganic or organocarboxylic acid having preferably 2 to 6 carbon atoms.

Among zinc salts of an inorganic acid mention may be made in particular of the chloride and the sulphate, but preferably zinc chloride.

Among the zinc salts of an organo-carboxylic acid having 2 to 6 carbon atoms mention may be made in particular of the acetate, the glycolate, the lactate, the gluconate and the citrate, but preferably zinc lactate and zinc citrate.

In accordance with a particularly preferred embodiment, the zinc salts are chosen from those which are soluble in water.

The selenium disulphide used in the compositions according to the invention essentially comprises one atom of selenium for every two atoms of sulphur. It may also have a polysulphide structure $Se_xS_y$ in which $x+y=8$.

Selenium disulphide is present in the form of a powder whose particles have a size of less than 200 mm and preferably less than 25 mm.

In the compositions according to the invention, selenium disulphide is preferably present in a proportion of between 0.001% and 5% by weight, and preferably between 0.25% and 2% by weight, relative to the total weight of the composition.

The zinc salt is generally present in a proportion of between 0.01% and 5% by weight, and preferably between 0.1% and 3% by weight, relative to the total weight of the composition.

According to a preferred embodiment of the compositions according to the invention, the ratio by weight of the zinc salt to selenium disulphide is between 0.1 and 3, and preferably between 0.2 and 2.

The compositions according to the invention can be presented in various forms. These forms include in particular shampoos or compositions for application before or after a shampoo, these compositions being present in the form of a lotion of greater or lesser thickness, a gel or an emulsion.

The compositions according to the invention, especially in shampoo form, additionally contain at least one anionic, nonionic, zwitterionic, amphoteric or cationic surfactant.

The proportion of the surfactant is generally between 0.01% and 50% by weight, but preferably between 0.05% and 30% by weight, relative to the total weight of the composition.

When a surfactant of the nonionic type is used, it is generally used in a proportion of between 0.1% and 40% by weight, and preferably between 1% and 20% by weight, relative to the total weight of the composition.

Surfactants of the cationic type, because of their low detergent power, are used more particularly in compositions according to the invention in the form of care hair compositions for use before or after shampooing.

Among the anionic surfactants which can be used, individually or in mixtures, according to the present invention mention may be made in particular of alkali metal salts, especially sodium salts, ammonium salts, amine salts, amino alcohol salts or magnesium salts, of the following compounds: alkyl sulphates, alkyl ether sulphates, alkylamido ether sulphates, monoglyceride sulphates, alkylglycerylsulphonates, alkylsulphonates, alkyl phosphates, alkylamidesulphonates, alkylarylsulphonates, α-olefinsulphonates, paraffinsulphonates, alkylsulphosuccinates, alkyl ether sulphosuccinates, alkylamidesulphosuccinates, alkylsulphosuccinamates, alkylsulphoacetates, alkyl ether phosphates, acyl isethionates, N-acyltaurates and N-acylamino acids such as N-acylsarcosinates and N-acylglutamates.

As anionic surfactants it is also possible to use salts of fatty acids, such as those of undecenylic, oleic, ricinoleic, palmitic and stearic acids, coconut oil acid or hydrogenated coconut oil acid, and of acyl-hydroxy acids such as acyllactylates.

It is also possible to use weakly anionic surfactants such as alkyl D-galactoside uronic acids and their salts, and polyoxyalkylenated ether carboxylic acids or their salts. The alkyl or acyl radical of the various surfactants listed above preferably has 8 to 22 carbon atoms.

Among nonionic surfactants mention may be made of polyethoxylated, polypropoxylated or polyglycerolated alcohols, α-diols, alkylphenols or fatty acids having a fatty chain containing 8 to 22 carbon atoms, the number of ethylene oxide or propylene oxide groups being able to range from 2 to 50 and the number of glycerol groups, in particular, from 2 to 30. Mention may also be made of copolymers of ethylene oxide and propylene oxide polyethoxylated amines or fatty amides with preferably 2 to 30 mol of ethylene oxide, polyglycerolated fatty amides containing on average 1 to 5 glycero groups, polyglycerolated diglycol amides, fatty acid esters of sorbitan, oxyethylenated or otherwise, fatty acid esters of sucrose, alkyl polyglycosides, oxyalkylenated or otherwise, alkyl glucoside esters, derivatives of N-alkylglucamine and amine oxides.

Among amphoteric or zwitterionic surfactants mention may be made of aliphatic secondary or tertiary amine derivatives in which the aliphatic radical is a linear or branched chain containing 8 to 22 carbon atoms and at least one anionic group which confers solubility in water (for example carboxylate, sulphonate, sulphate, phosphate or phosphonate) such as, for example, alkylbetaines, alkylaminocarboxylates, sulphobetaines, alkylamidoalkylbetaines, alkylamidoalkylsulphobetaines, and imidazolium derivatives, especially those of amphocarboxyglycinate or amphocarboxypropionate.

Among cationic surfactants mention may be made in particular of fatty amine salts, polyoxyalkylenated and/or quaternized or otherwise, esters of fatty acids and amino alcohols, polyoxyalkylenated and/or quaternized or otherwise, quaternary ammonium salts such as tetraalkylammonium bromides or chlorides, alkylamidoalkyltrialkylammonium chlorides or bromides, trialkylbenzylammonium chlorides or bromides, trialkylhydroxyalkylammonium chlorides or bromides, dialkylamidoalkyldimethylammonium chlorides or bromides, alkylpyridinium chlorides or bromides and imidazolium derivatives.

The aqueous vehicle of the compositions according to the invention is either water or a mixture of water and a cosmetically acceptable solvent such as ethanol, glycol or a glycol ether.

The compositions according to the invention can also contain at least one cosmetically or dermatologically acceptable additive chosen from a conditioner, a thickener, a cationic, anionic, nonionic or amphoteric polymer, a sunscreen, a ceramide, an α-hydroxy acid, a preservative, an antimicrobial agent, an additional anti-dandruff agent, a pearlescent agent, a colorant, a fragrance, an electrolyte or a suspending agent.

As conditioner which can be used in the compositions according to the invention particular mention may be made of natural oils, hydrogenated or otherwise, synthetic hydrocarbon, cyclic or aliphatic, linear or branched, saturated or unsaturated oils, such as, for example, poly-α-olefins, especially polydecenes and polyisobutenes, volatile or nonvolatile, soluble or insoluble silicone oils which are organically modified or otherwise, fluorinated or perfluorinated oils, fatty esters, esters of polyhydric alcohols and glycerides.

Other conditioners which can be used in the compositions according to the invention are synthetic or natural waxes, silicone resins and gums, proteins or protein hydrolysates, quaternized or otherwise, or a mixture of these various agents.

The additives are generally present in the compositions according to the invention in a proportion of between 0.01% and 20% by weight, and preferably between 0.02% and 10% by weight, relative to the total weight of the composition.

The pH of the compositions according to the invention is generally less than 7 and preferably between 3 and 4.5.

Another subject of the present invention is a method of cosmetic treatment comprising the application to the hair of a sufficient quantity of a composition as defined above.

In general, the composition is applied 1 to 3 times a week for 6 to 8 weeks.

When the composition according to the invention is applied in the form of a lotion or cream for use before or after shampooing, it can optionally be left to act on the hair for approximately ½ to 5 minutes before optional rinsing with water is carried out.

A number of examples of anti-dandruff hair compositions according to the invention will now be given by way of illustration.

EXAMPLE I: Anti-dandruff shampoo

| | |
|---|---|
| Selenium disulphide | 0.25 g |
| Zinc chloride | 0.1 g |
| Oxyethylenated lauryl ether sulphate of sodium and magnesium (80/20) containing 4 mol of ethylene oxide, sold under the name "Empicol BSD" by the company Albright and Wilson | 10 g AS |
| Cocoylamidopropylbetaine/glycerol monolaurate mixture, sold under the name "Tégobétaine-HS" by the company Goldsmidt in aqueous solution containing 30% AS | 5 g AS |
| Polydimethylsiloxane (MW 250,000) sold under the name "Silbione huile 70047 V 500.000" by the company Rhone Poulenc | 2 g |
| Mixture of cetyl 2-hydroxycetylstearyl ether and cetyl alcohol (60/40) | 2.5 g |
| Coconut acid monoisopropanolamide | 1.5 g |
| Crosslinked acrylic acid-($C_{10}$–$C_{30}$)alkyl acrylate copolymer sold under the name "Carbopol 1382" by the company Goodrich | 0.5 g |
| NaOH qs | pH 4 |
| Water qs | 100 g |

The resulting shampoo, when placed in an oven at 45° C. for 1 month, shows no change in colour and retains its anti-dandruff activity.

A shampoo the same as above but without zinc chloride undergoes a rapid change in colour, passing from light orange to dark brown.

After wetting the hair, a sufficient quantity of the shampoo is applied, foamed and allowed to act for about 2 minutes. The hair is then rinsed thoroughly. Used regularly, this shampoo enables the elimination, and prevention of the reappearance, of dandruff.

EXAMPLE II: Anti-dandruff shampoo

| | |
|---|---|
| Selenium disulphide | 1 g |
| Zinc chloride | 0.4 g |
| Polyglycerolated dodecanediol containing 3.5 mol of glycerol | 20 g AS |
| Perhydrosqualene | 2 g |
| Xanthan gum | 1 g |
| Preservative | qs |
| Fragrance | qs |
| Hydrochloric acid qs | pH 4 |
| Water qs | 100 g |

EXAMPLE III: Anti-dandruff shampoo

| | |
|---|---|
| Selenium disulphide | 1 g |
| Zinc lactate | 0.1 g |
| Oxyethylenated lauryl ether sulphate of sodium and magnesium (80/20) (Empicol BSD) | 10 g |
| Cocoylamidopropylbetaine/glycerol monolaurate mixture (Tégobétaine-HS) | 5 g AS |
| Polydimethylsiloxane (Silbione huile 70047 C 500.000) | 2 g |

-continued

| | |
|---|---|
| Crosslinked acrylic acid ($C_{10}$–$C_{30}$) alkyl acrylate copolymer (Carbopol 1382) | 0.5 g |
| Mixture of cetyl 2-hydroxycetyl stearyl ether/cetyl alcohol (60/40) | 2.5 g |
| Coconut acid monoisopropanolamide | 1.5 g |
| NaOH qs | pH 4 |
| Water qs | 100 g |

EXAMPLE IV: Anti-dandruff composition for use after shampooing

| | |
|---|---|
| Selenium disulphide | 1 g |
| Zinc chloride | 1 g |
| Polyacrylamide sold under the name "Sepigel 305" by the company Seppic | 3 g AS |
| Cyclomethicone (and) dimethiconol sold under the name "Dow Corning 1401 Substantivity Aid Fluid" by the company Dow Corning | 20 g |
| Hydrochloric acid qs | pH 4 |
| Water qs | 100 g |

EXAMPLE V: Anti-dandruff composition for use after shampooing

| | |
|---|---|
| Selenium disulphide | 0.5 g |
| Zinc citrate | 0.3 g |
| Polyacrylamide ("Sepigel 305") | 3 g AS |
| Diphenyldimethicone sold under the name "Silbione Oil 70641 V 200" by the company Phone-Poulenc | 5 g |
| Preservative qs | |
| Fragrance qs | |
| Hydrochloric acid qs | pH 4 |
| Water qs | 100 g |

After having thoroughly rinsed hair which has been shampooed beforehand, a sufficient quantity of one of the compositions of Examples IV and V is applied to the entire hair. It is left to act for approximately 2 to 5 minutes and then, after rinsing if appropriate, the hair is styled.

We claim:

1. A stable cosmetic, dermatological or pharmaceutical composition comprising, in an aqueous medium, selenium disulphide in a mixture with at least one zinc salt of an inorganic or organo-carboxylic acid.

2. The composition according to claim 1, wherein said zinc salt of an inorganic acid is selected from the group consisting of zinc chloride and zinc sulphate.

3. The composition according to claim 1, wherein said zinc salt of an organo-carboxylic acid is selected from the group consisting of zinc acetate, zinc glycolate, zinc lactate, zinc gluconate and zinc citrate.

4. The composition according to claim 1, wherein selenium disulphide is present in a proportion of between 0.001% and 5% by weight, relative to the total weight of the composition.

5. The composition according to claim 4, wherein the proportion of selenium disulphide is between 0.25% and 2% by weight, relative to the total weight of the composition.

6. The composition according to claim 1, wherein said zinc salt is present in a proportion of between 0.001% and 5% by weight, relative to the total weight of the composition.

7. The composition according to claim 6, wherein the proportion of zinc salt is between 0.1% and 3% by weight, relative to the total weight of the composition.

8. The composition according to claim 1, wherein the ratio by weight of the zinc salt to selenium disulphide is between 0.1 and 3.

9. The composition according to claim 8, wherein said ratio is between 0.2 and 2.

10. The composition according to claim 1, which additionally contains at least one anionic, nonionic, zwitterionic, amphoteric or cationic surfactant in a proportion of between 0.01% and 50% by weight, relative to the total weight of the composition.

11. The composition according to claim 1, which additionally contains at least one additive selected from the group consisting of a conditioner, a thickener, a cationic, anionic, nonionic or amphoteric polymer, a sunscreen, a ceramide, an α-hydroxy acid, a preservative, an antimicrobial agent, an additional anti-dandruff agent, a pearlescent agent, a colorant, a fragrance, an electrolyte and a suspending agent.

12. A method of treatment, wherein a sufficient amount of a composition according to claim 1 is applied to the hair.

13. The method according to claim 12 for the treatment of dandruff.

14. A process to stabilize an aqueous composition containing selenium disulphide, said process comprising adding to said composition at least one zinc salt of an inorganic or organo-carboxylic acid.

* * * * *